United States Patent
Steffier et al.

(10) Patent No.: US 8,684,739 B2
(45) Date of Patent: Apr. 1, 2014

(54) DURABLE FILM COATING COMPOSITIONS HAVING SUSTAINED SLOW-RELEASE CAPABILITY, AND METHODS OF USE THEREFOR

(75) Inventors: Larry W. Steffier, Cherry Hill, NJ (US); David Kurz, Swedesboro, NJ (US); Robert R. Raney, Newtown Sq., PA (US); Cary B. Robinson, Cherry Hill, NJ (US)

(73) Assignee: Mycone Dental Supply Co., Inc., Cherry Hill, NJ (US)

( * ) Notice: Subject to any disclaimer, the term of this patent is extended or adjusted under 35 U.S.C. 154(b) by 450 days.

(21) Appl. No.: 10/389,501

(22) Filed: Mar. 14, 2003

(65) Prior Publication Data

US 2003/0175347 A1 Sep. 18, 2003

Related U.S. Application Data

(60) Provisional application No. 60/364,266, filed on Mar. 14, 2002.

(51) Int. Cl.
*A61K 9/52* (2006.01)

(52) U.S. Cl.
USPC ............ 434/100; 424/475; 424/473; 106/240

(58) Field of Classification Search
USPC ............. 424/489, 497, 502, 468, 470; 435/4, 435/7.1, 14
See application file for complete search history.

(56) References Cited

U.S. PATENT DOCUMENTS

| | | | | |
|---|---|---|---|---|
| 2,969,330 | A | 1/1961 | Brynko | 252/316 |
| 3,137,631 | A | 6/1964 | Soloway | 167/83 |
| 3,341,466 | A | 9/1967 | Brynko et al. | 252/316 |
| 3,415,758 | A | 12/1968 | Powell et al. | 252/316 |
| 3,516,943 | A | 6/1970 | Brynko et al. | 252/316 |
| 3,531,463 | A | 9/1970 | Gustafson | 260/211.5 |
| 3,615,972 | A * | 10/1971 | Morehouse et al. | 156/79 |
| 4,221,871 | A | 9/1980 | Meitzner et al. | 521/29 |
| 4,224,415 | A | 9/1980 | Meitzner et al. | 521/38 |
| 4,690,825 | A * | 9/1987 | Won | 424/501 |
| 4,844,885 | A | 7/1989 | Chernack | 424/61 |
| 5,145,675 | A * | 9/1992 | Won | 424/78.31 |
| 5,154,939 | A * | 10/1992 | Broderick et al. | 426/5 |
| 5,837,226 | A * | 11/1998 | Jungherr et al. | 424/78.1 |
| 5,849,327 | A * | 12/1998 | Berliner et al. | 424/463 |
| 5,861,142 | A * | 1/1999 | Schick | 424/61 |
| 5,922,334 | A | 7/1999 | Krasnansky et al. | 424/401 |
| 6,323,249 | B1 | 11/2001 | Dale et al. | 521/38 |
| 6,696,258 | B1 * | 2/2004 | Wei et al. | 435/7.2 |
| 2001/0007676 | A1 * | 7/2001 | Mui et al. | 424/401 |
| 2002/0037298 | A1 * | 3/2002 | Allwohn et al. | 424/401 |
| 2003/0149090 | A1 * | 8/2003 | Gehlsen et al. | 514/400 |

FOREIGN PATENT DOCUMENTS

EP 0135292 3/1985

OTHER PUBLICATIONS

Mui et al., International Journal of Cosmetic Science 22:121-131 (2000).*
Santa Maria et al., Materials Letters 58:563-568 (2004).*
Danumah et al (2001 Microporous and Mesoporous Materials 44-45 pp. 241-247).*
Bellobono et al., *J. Applied Polymer Sci.*, 29:3185-3195 (1984).
*Encyclopedia of Chemical Technology*, vol. 13, J. A. Herbig, "Microencapsulation", pp. 436-456, John Wiley & Sons, Inc. 2$^{nd}$ Edition, 1967.
Mui et al., "Evaluation of New Plasticizers for use in Nail Enamel". XIII I.E.S.C.C. Internat'l Conf., Acapulco, Mexico, 1997.
Mui et al., Tevco, Inc. publication O17. "The Development of "Time Release" Nail Enamels"; presented at XIII I.E.S.C.C. Internat'l Conf., Acapulco, Mexico, 1997.
Deleuzel, "Porosity analysis of som poly9styrene/divinylbenzene)beads by nitrogen sorption and mercury intrusion porosimetry," Polymer Bulletin 44:179-186, 2000.
Kang, "Effect of Solvent on Pore Characteristics of Styrene-Divinylbenzene Copolymer," Polymer(Korea), 23(3):368-375, 1999, English Abstract Only.

* cited by examiner

*Primary Examiner* — Christopher M Gross
(74) *Attorney, Agent, or Firm* — Michael B. Fein, Esq.; Eckert Seamans Cherin & Mellott, LLC

(57) ABSTRACT

Provided is a slow-release delivery vehicle for delivering at least one active ingredient into a film coating, comprising a population of stable, homogeneously-dispersed, porous polymeric or co-polymeric beads having a network of pores, wherein the at least one active ingredient is held within the bead particles and within the network of pores and slowly released by internal flow, and wherein the network of pores is substantially non-collapsible upon removal of the active ingredient. The porous co-polymer bead preparation comprises a continuous aqueous phase solution containing a monomeric mixture of at least one polyvinylaromatic monomer and at least one porogen forming a network that comprising (i) macropores; (ii) mesopores; (iii) micropores; and (iv) gel porosity. Also provided are methods of preparing the porous co-polymer bead preparation; and for its use as a slow-release delivery vehicle.

15 Claims, 2 Drawing Sheets

DURABLE FILM COATING COMPOSITIONS HAVING SUSTAINED SLOW-RELEASE CAPABILITY, AND METHODS OF USE THEREFOR

REFERENCE TO RELATED APPLICATION

This application claims priority to U.S. Provisional Application No. 60/364,266, filed Mar. 14, 2002, the content of which is herein incorporated by reference.

FIELD OF THE INVENTION

The present invention provides durable film coating compositions and methods of use therefore comprising controlled, slow, sustained release of an active ingredient into the dried coating.

BACKGROUND OF THE INVENTION

Various types of polymeric and co-polymeric coating compositions are used by consumers today, ranging from paints and varnishes for cars, boats and homes to topical applications for skin or nail coatings. In fact some, polymer coatings actually are prepared as sheet material, such as a shower curtain. However, they have in common a need to provide a fluid delivery that dries as a smooth, durable surface, capable of withstanding exposure to sun, light, air, moisture, heat, cold and chemicals present in the environment without becoming brittle and chipping, spalling, cracking, shattering or disintegrating, especially when subjected to external physical stress or movement.

Drying, setting, or curing time and durability are two of the most important characteristics of film coating compounds. As drying time is decreased, durability may be adversely affected. As a result, a balance of resins, plasticizers, polymers, catalysts, curing agents and solvents are selected and used to permit rapid drying and/or curing, but also to maintain the dried film in a dynamic and somewhat flexible state for as long as possible, while at the same time providing a hard, durable, smooth coat that will resist denting and abrasion. The plasticizers typically added to polymeric compositions, often with other components, are used to counteract the effects of aging and to enhance durability and flexibility of the coating. However, plasticizers tend to become volatile at ambient temperatures. Consequently, a substantial amount of plasticizer flashes from the substrate, along with the solvents, as the film dries. Moreover, the remaining plasticizer component continues to volatilize, particularly at the coating/air interface, and molecules are steadily released from the dried coating into the air, soon leaving the coating dry and brittle.

Using nail coating compositions as an example, the polymeric coatings typically contain one or more film formers in combination with other formulation additives, such as solvents, coalescent agents, plasticizers, thickeners, suspension aids, and pigments. Nitrocellulose, is often used in combination with a secondary film former, such as toluene sulfonamide formaldehyde, to improve properties, such as application, wear, and gloss. Nevertheless, although nitrocellulose has excellent pigment wetting capabilities, and forms a film, which dries quickly, has high gloss, good hardness, and good resistance to abrasion and chemicals, it has disadvantages. For example, formulations containing nitrocellulose tend to discolor the nails, and over time tend to drop in viscosity and may lose the ability to form a hard film. Also, for solubility reasons, nitrocellulose is undesirably formulated with organic solvents, such as ethyl acetate, methyl ethyl ketone, and toluene. The organic solvents, however, also tend to discolor the nails, and make them brittle. Therefore, a plasticizer component acts to combat brittleness, but any plasticizer added to the coating must also withstand the drying effect of the solvents.

Other approaches utilize a blend or dispersion of polymers, which will form a film from an aqueous medium, e.g., polyurethane or polyacrylate compositions. However, these polymers tend to have inferior pigment wetting properties, and form films which are not durable, and have poor resistance to chemicals and abrasion. Accordingly, the present invention addresses these problems by incorporating into an aqueous nail coating composition, agents, such as a plasticizing agent, which is continuously released in a controlled manner into the post-application, dried film coating.

To facilitate continuous or controlled release, two major types of micropackaging or microcontainment systems have been developed for packaging and containing active liquids, fluids and solids in the form of free-flowing beads, particles, or powders. In entrapment systems, the active liquid, ingredient, or functional material is contained by sorption within a microscopic polymeric matrix or lattice. The polymer lattice containment results in conversion, for example, of liquids, waxes, or solids into free-flowing particles. By comparison, in microencapsulation, small droplets of the active or functional liquid or solid are coated with a continuous film of polymeric material. The process of microencapsulation and formation of microcapsule systems is further described in the *Encyclopedia of Chemical Technology*, Vol. 13, J. A. Herbig, "Microencapsulation", pp. 436-456, John Wiley & Sons, Inc., 2nd edition, 1967, and various United States patents including U.S. Pat. Nos. 2,969,330, 3,137,631, 3,341,466, 3,516,943 and 3,415,758.

Micropackaging by encapsulation or entrapment protects the active liquids or solids from deterioration and exposure to air or even light, and increases longevity. Typical polymer entrapment particles range in particle size from less than 0.10 microns to, for example, 5,000 microns, that is from powders to beads. The characteristics of the entrapment materials may be varied according to the lattice wall co-polymers and the ratio or percentage of co-polymers comprising the particles. Inorganic or organic hollow, spherical polymeric powders, sized under 1000 microns, are often referred to as "microspheres."

Rohm and Haas Co. developed a Meitzner-Oline portfolio of technologies for producing polymerization processes and products therefrom, including U.S. Pat. Nos. 3,531,463; 4,224,415 and 4,221,871. In general, the patents teach that a resin forms a matrix of solid co-polymer, having a macroreticular structure, which is permeated by small channels or voids into which liquids can penetrate. The resulting co-polymeric ionic resin complex, particularly when cross-linked, is effective for absorbing organic fluids or separating mixtures of organic fluids. The matrix is formed by the suspension co-polymerization of a monovinyl carbocyclic aromatic compound or an ester of acrylic or methacrylic acids, with a polyethylenically unsaturated monomer dissolved in a organic liquid—of mixture of organic liquid-solvent. A high degree of cross-linking of the polymerized monomer results in an enhanced macroreticular structure with many small channels, and also provides enhanced durability. Other patents such as U.S. Pat. No. 6,323,249, as well as the references cited therein, provide additional teaching in the art that may be used for comparative purposes.

The microchannels formed by the Meitzner-Oline process are separate and distinct from the micropores formed in by other cross-linked polymers. During formation of the copolymer, solubility of the monomer of the co-polymer is decreased as precipitant is added during phase separation of the monomer phase. As a result as the concentration of co-polymer increases and the concentration of monomer decreases, as compared to the co-polymerizing mass. Thus, the precipitant is repelled by the co-polymer and actually squeezed out of the co-polymer phase, leaving the series of microchannels.

U.S. Pat. No. 4,690,825 (Applied Polymer Systems, Inc.) teaches a method for the sustained release delivery of impregnated materials for topical application, including vitamins, steroids, insect repellents, ultraviolet absorbents, hair growth promoters, acne treatments and fragrances, alone or from a carrier or cosmetic solid. The delivery vehicles are polymeric beads formed by a polymerization process in which the active material is the porogen during the pore forming process. As, a result, the active material is trapped and held within the substantially non-collapsible pore network. Along with related patents U.S. Pat. Nos. 5,145,675 and 5,955,109, the polymeric controlled release delivery system comprises the materials and methods used in the controlled release delivery of active substances.

Optimally, the active ingredient particles in the Applied Polymer Systems' processes are spherical in shape ranging from about 0.10 to 100 microns in diameter, imparting a smooth feel, prepared by suspension polymerization in a liquid-liquid system. A solution is formed by polymerizing one or more polymers by a free radical suspension polymerization process, and the active ingredient is delivered from the macropores formed therein. However, no delivery is made from the polymerized particles or the micro- or mesopores formed during the polymerization process.

U.S. Pat. No. 4,844,885 (Chemack) teaches a composition containing pressure-sensitive microcapsules, wherein the composition comprises a liquid phase capable of solidification, e.g., as a nail lacquer. Substantially evenly dispersed throughout the liquid phase is a multiplicity of microencapsulated droplets of a solvent phase. The shells of the microcapsule are ruptured under applied pressure for selectively releasing the solvent phase, e.g., nail lacquer remover, for dissolving the liquid phase after it has solidified.

U.S. Pat. No. 5,922,334 (Krasnansky et al.) provides an aqueous nail coating composition comprising: at least one film forming agent comprising a dispersion of multi-phase polymers; wherein the multi-phase polymers comprise at least one inner polymer phase and at least one outer polymer phase; wherein the inner polymer has a Tg of at least 30° C. and comprises as polymerized units at least 2 weight percent of a hydrophobic monomer, based on total weight of monomer in the inner polymer; wherein the outer polymer has a Tg from −15° C. to 35° C., and comprises as polymerized units at least 3 weight percent of a second hydrophobic monomer; wherein the weight ratio of the inner polymer to the outer polymer is from 20:80 to 70:30; and provided that when the outer polymer has a weight average molecular weight equal to or greater than 200,000, the inner polymer further comprises at least 0.01 weight percent cross-linking agent based on total monomer in the inner polymer, and the outer polymer has a soluble fraction in tetrahydrofuran of at least 15 weight percent, and comprises from 3 weight percent to 70 weight percent of the second hydrophobic monomer based on total monomer in the outer polymer.

None of the prior art coating compositions have been able to exhibit durability during wear, which prevents the coating from hardening and becoming more brittle, which invariably results in the cracking and breaking of the film coated surface. In particular, in the nail coating industry, the prior art continues to search for a coating that provides a high gloss, defined color, long wear and chip resistance, and yet retains nail flexibility, durability, resistance to abrasion and chipping, and adherence without brittleness over extended periods of time.

SUMMARY OF THE INVENTION

The present invention provides a slow-release delivery vehicle for delivering at least one active ingredient into a film coating, comprising a population of stable, homogeneously-dispersed, porous polymeric or co-polymeric beads having a network of pores, wherein the at least one active ingredient is held within the bead particles and within the network of pores and slowly released by internal flow, and wherein the network of pores is substantially non-collapsible upon removal of the active ingredient. It is an object, therefore, to provide, such delivery vehicle of claim 1, wherein the network of pores comprises (i) macropores; (ii) mesopores; (iii) micropores; and (iv) gel porosity. The porous co-polymer bead preparation comprises a continuous aqueous phase solution containing a monomeric mixture, further comprising at least one polyvinylaromatic monomer and at least one porogen.

In preferred embodiments of the invention, the composition may be cross-linked, comprising polyethylenically unsaturated cross-linking monomers.

In additional embodiments, of the invention an active ingredient comprises at least one plasticizer. Further embodied are compositions comprising at least one film forming ingredient, and/or any of a number of additional active ingredients that benefit the composition itself (mechanical, physical or chemical characteristics) and/or that upon slow and continuous release from the present composition will benefit the surface over which the coating is applied.

It is a further object of the invention to provide a method for preparing slow-release delivery vehicle for delivering at least one active ingredient into a film coating, comprising the steps of: dissolving at least one monomeric composition in an inert porogen to form a solution; suspending the solution in a phase incompatible with the solution; agitating the solution and the phase to form a plurality of droplets of the solution suspended in the phase; activating at least one monomer in the plurality of droplets to polymerize the at least one monomeric composition and form a population of stable, homogeneously-dispersed, porous polymeric or co-polymeric beads having a network of pores, capable of containing at least one active ingredient within the bead particles and within the network of pores and slowly releasing same by internal flow, and wherein the network of pores is substantially non-collapsible upon removal of the active ingredient; separating the porous polymeric bead from the phase; removing any impurity from the porous polymeric bead; and adding at least one active ingredient to the porous polymeric bead preparation to form the delivery vehicle. In at least one preferred embodiment, the method of preparation of the porous co-polymer bead preparation further comprises mixing in aqueous phase solution a monomeric mixture, which further comprising at least one polyvinylaromatic monomer and at least one porogen. Further, the mixture may involve at least partial cross-linking to form the porous bead.

It is yet another object of the invention to provide a system or method for delivering an active ingredient into a film coating of claim 1 by slow-release delivery, comprising the steps of: mixing a delivery vehicle with a medium to form a mixture, which comprises at least one active ingredient, and wherein the delivery vehicle comprises a population of stable, homogeneously-dispersed, porous polymeric or co-polymeric beads having a network of pores, capable of containing at least one active ingredient within the bead particles and within the network of pores and slowly releasing same by internal flow, and wherein the network of pores is substantially non-collapsible upon removal of the active ingredient; applying the mixture to a surface; and releasing the at least one active ingredient from the network of pores and bead particles. In at least one embodiment, the method of delivery from the porous co-polymer bead preparation comprises a continuous aqueous phase solution containing a monomeric mixture, further comprising at least one polyvinylaromatic monomer and at least one porogen. Further, at least one monomer is at least partially cross-linked to form the porous bead.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures.

DETAILED DESCRIPTION OF PREFERRED EMBODIMENTS

Figure 1:
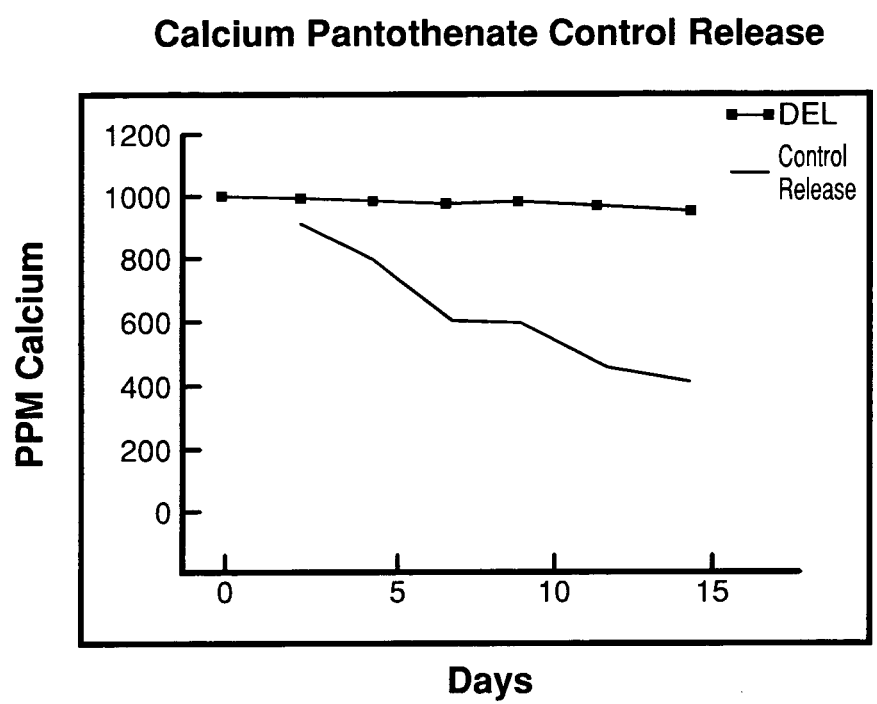
FIG. 1 graphically shows the controlled release delivery of a non aromatic compound, calcium pantothenate ($C_9H_{17}NO_5 \cdot \frac{1}{2}Ca$), over a time course of 15 days.

The present invention provides compositions and methods for the controlled, sustained release of one or more active ingredients from a film coating composition comprising a rigid, open-pore network, wherein the network comprises (i) particles and (ii) a pore network within a polymerized bead or microsphere, and wherein the "pore network" comprises macropores, mesopores, micropores, and gel porosity. The pore network is substantially interconnected and open to the surface of the polymerized bead or microsphere.

The terms "bead" or "microsphere" are used interchangeably herein to refer to the polymerized unit forming a matrix of interconnecting particles ("gel" or "gel particles") and pores (the pore network). The terms, selected to designate the generally round shape of the polymerized body, are not intended to be definitive of the geometric character of the porous bodies. However, in general, spherical beads tend to provide a smoother coating material than angular shards, and the intent of the method is to provide a coating that, in addition to other definitive characteristics, is smooth and free flowing during application as a liquid.

In operation, the macropores rapidly release the active ingredient, contained therein as a plurality of molecules, from the polymerized bead or microsphere into the film coating by methods known in the art. However, in accordance with the present invention, the delivery method relies upon several interacting principles—the fact that the active molecules within the system continuously replenish the macropores for release into the coating, and the fact that at the same time there is a long term, sustained controlled release from the remainder of the pore network. Thus, the present invention is unique, and distinguished from delivery systems in the prior art. In the presently disclosed system, the active ingredient, contained as a plurality of molecules within the gel, i.e., within the gel particles (also referred to as a "microgel" or "microparticles") is slowly released as a continuous process into and from the pore network. Finally, the active ingredient contained as a plurality of molecules within the micropore network, is very slowly released as a continuous process presumably into the mesopores, and then into the macropores, from which it is then released as above. The actual mechanism is not fully understood at the present time. In the alternative, when the film coats a surface, the release of the active ingredient can be directed into the coated surface, such as the painted material, or on a human, the skin or nail.

An interesting phenomenon has been reported in film coatings that are applied or formed as a liquid. Even after the coating has dried, an internal flow persists. By "internal flow" is meant an area that develops beneath film surface (the coating/air interface) as the coating dries, wherein the film components remain dynamic and mobile (Mui et al., Tevco, Inc. publication O17; Mui et al., XIII I.F.S.C.C. Internat'l Conf., Acapulco, Mexico, 1997)). Although directly related to the balance of resins (type and grade), plasticizers, polymers and solvents used in the coating, the longer the internal flow persists, the more durable the coating will be, in terms of crack and abrasion resistance. Film performance is gauged by elongation, tensile strength, and tensile modulus.

By "active ingredient" is meant a substance less than approximately 2000 daltons that will benefit the substrate or the coating composition in which the material is placed. Examples of active ingredients that may benefit the coating material and or substrate include, but are not limited to, plasticizers, pigments, dyes, stabilizing agents such as UV absorbers and blockers, brighteners, fragrances, flavors, opacifiers, oils, moisturizers, antioxidants, solvents, bactericides, mildewcides, fungicides, herbicides, pesticides, vitamins, stabilizing agents such as inhibitors and or radical traps, antibiotics, antimicrobials, slip agents, and catalysts, and the like. It is also contemplated that the invention is useful for delivery of or stabilizing antibiotics, antimicrobials, therapeutic drugs, radiation treatment and imaging materials.

Polymeric Bead or Microsphere Systems for Controlled Release of Active Ingredient In a preferred embodiment of the present invention, a delivery vehicle comprises a polymeric bead having a network of pores with the active ingredient held within the network is utilized to provide a controlled time release of the active ingredient. The active ingredient is selected from any of the following: a plasticizer, a lubricant, an emollient, a moisturizer, a pigment, an insect repellant, a fragrance, a vitamin, a drug, botanical, or any combination thereof, or any other functional ingredient. In a particularly preferred embodiment, it is a plasticizer.

The delivery vehicle is incorporated in a fluid medium, such as a gel, a cream, a lotion, an ointment, a liquid or the like, which may then be applied to a surface. The active ingredient is released by pressure, diffusion or volatilization (methods which are well characterized in the art)(see, e.g., Bellobono et al., *J. Applied Polymer Sci.*, 29:3185-3195 (1984). Thus, the delivery vehicle is uniquely suited for use in a wide variety of applications in which it is desirable to release an active ingredient by one or more methods.

A delivery vehicle according to the present invention has increased mechanical stability over a microencapsulated vacuole-type delivery vehicle. The network of pores of a bead according to the present invention will not be subject to osmotic shock, which might occur in prior art delivery vehicles. In addition, the increased mechanical stability allows a delivery vehicle to be manufactured, processed and handled under more severe conditions, such as mechanical stirring, which might otherwise rupture or damage prior art gel or microencapsulated delivery vehicles. Thus, a delivery vehicle according to the present invention can easily be incorporated in various coating media, in which, by comparison, it would prove difficult or more expensive to incorporate delivery vehicles of the prior art.

When a delivery vehicle is prepared in accordance with the present invention, the active ingredient is trapped both within (i) the particles, and (ii) the network, of pores formed during polymerization of the bead. Thus, in contrast to a process wherein an active ingredient is absorbed into a preformed matrix, the active ingredient in a delivery vehicle of the present invention should have a substantially uniform concentration throughout the network of particles and pores. In fact, the delivery vehicle of the present invention comprises a pore structure that is itself at least a four-part element, comprising (i) macropores (defined as >500 Å); (ii) mesopores (defined as >20 Å to <500 Å); (iii) "micropores," (defined as <20 Å); and (iv) "gel porosity" (defined as ≤approximately 40 Å).

The macropores provide an environment enabling fast or quick delivery of an active ingredient. The mesopores provides for slower than macropore delivery, but faster than micropore and gel pore delivery. Combined micropore and microgel delivery permits for the extended delivery time for up to months or years. Although the mechanisms of delivery are not fully understood at this time; by changing the relative contents of the various pore regimes, as well as the polymeric composition, the methods of the present invention permit control over the rate of release from the delivery vehicle into a receiving substrate.

The active ingredient is held within the pore network simply by van der Walls forces or ionic bonding. No covalent bonding of the materials is involved in the present invention.

The delivery vehicle of the instant invention is capable of providing sustained release of the active ingredient over a period of time, as compared to a rapid, total release using microencapsulated delivery. Moreover, by achieving uniformity, a more controlled time release of the active ingredient is created than would be possible from prior art systems in which the delivery is made from only the network of macropores over a given period of time. For example, in U.S. Pat. No. 4,690,825, described above, a delivery vehicle is taught comprising a polymeric bead having a network of pores with an active ingredient held within and released from the network of substantially non-collapsible pores. The '825 delivery vehicle is polymerized by a process in which the active ingredient also comprises the porogen during formation of the network of pores. However, the active material in the '825 patent is delivered only from the macropores; no delivery is made from the remainder of the pore system or the gel particles, nor is it suggested that such delivery is contemplated or even possible.

The active ingredient, whether pure (solid) active ingredient, a mixture of active ingredients or a solution of active ingredient(s) in the present invention, generally comprises amounts ranging from traces of an active ingredient to the maximum capacity of a particular polymeric system. Thus, the maximum capacity in a preferred embodiment could be as high as approximately 90 grams of dibutyl phthalate and 10 grams of polymer matrix using 100 grams of polymeric vehicle. Generally the delivered active ingredient, in accordance with the present invention, could range between approximately <1% and approximately >20% of the total weight of the impregnated beads. Preferably it comprises from about <1% to 10%, more preferably from about 1% to 5%, most preferably from 1% to 2.5% of the total weight.

A delivery vehicle as embodied in the present invention (e.g., beads or microspheres) is prepared by polymerizing one or more monomers by a free radical suspension polymerization process in a liquid-liquid system. In general, monomer(s) or co-monomer(s) are dissolved in an inert porogen, which is also the active ingredient, to form a solution, which is suspended in a phase or solvent incompatible with the solution, along with a polymerization catalyst (if used). As a result, an inert but fully miscible liquid is formed which is immiscible with water. The solution is then suspended in an aqueous solution, which generally contains additives, such as surfactants and dispersants to promote the suspension.

After the active ingredient is dissolved or suspended in the liquid phase (i.e., the suspension is established by agitation or sonication to form a plurality of droplets of the desired size of solution suspended in the liquid phase), the monomer(s) or co-monomers in the plurality of droplets are activated to initiate a polymerization reaction in which a monomer (or co-monomer) is cross-linked, or two or more monomers are polymerized to form porous beads having a network of pores. Activation is spontaneous upon agitation, or it is triggered by an initiator or catalyst, such as an azo catalyst, which is soluble in the monomer solution. If an initiation catalyst is used, it must be one that does not oxidize or denature the active ingredient. Alternatively, although polymerization temperatures are optimally within a moderate range, activation may also be triggered by an energy source, such as heat or radiation. Several mechanisms may be combined to enhance activation of polymerization. Surfactants or wetting agents may also be added.

Once polymerization is complete, the resulting rigid beads are recovered from the suspension. The beads at this point are solid porous structures, the polymer having formed around the inert, substantially water-immiscible liquid, thereby forming the pore network. The liquid has accordingly served as a porogen, (note that the porogen can also be a polymer as discussed, e.g., in U.S. Pat. No. 6,323,249) or pore-forming agent, and occupies the pores of the formed beads. The porogen is inert and nonreactive with the active material. However, in an alternative embodiment, a portion of, or all of the porogen, comprises the active ingredient held within the network of pores, and a portion is held within the polymerized particles forming the network.

The "porogen" of the present invention is defined as a substance that imparts porosity into a cross-linked polymerization system when added to monomer(s) before gelation occurs. In some cases, such as the case of dibutyl phthalate (DBP), the active ingredient is also the porogen. The inert porogen serves as an internal diluent during polymerization to introduce the desired macroporous structure or network of pores into the finished delivery vehicle. The inert porogen should not react with the monomer present during polymerization or inhibit the polymerization. The bead of the delivery vehicle may or may not swell with the inert porogen.

The determination of the most effective precipitant and the amounts required for the formation of a particular co-polymer may vary from case to case because of the numerous factors involved. However, although no "universal" or single class of precipitants is applicable to all cases, it is well within the skill of one of ordinary skill in the art to determine without much difficulty which precipitants will be effective in a given situation. The requirements of solubility with the monomer mixture and low or non-solubility in the co-polymer can be tested empirically using known methods, and the solubilities of many monomers and co-polymers are published information in manuscripts and textbooks.

A typical macroporous co-polymer preparation of an embodiment of the present invention, for example, may include a preparation of a continuous aqueous phase solution containing suspension aids (such as, dispersants, protective colloids and buffers) followed by mixing with a monomeric mixture containing 50% to 100% polyvinylaromatic monomeric, free-radical initiator and 2 to 5 parts porogen (such as, toluene, xylenes, ($C_4$-$C_{10}$)-alkanols, ($C_6$-$C_{12}$)-saturated hydrocarbons or polyalkylene glycols) per one part monomer. The mixture of monomers and porogen is optimally polymerized at elevated temperature, and the porogen is subsequently removed from the resulting polymer beads by various means. For example, toluene, xylene and ($C_4$-$C_{10}$)-alcohols may be removed by distillation or solvent washing, and 20 polyalkylene glycols by water washing. The selection of the washing solvent, e.g., whether water or organic, is within the skill of one familiar with the art. The resulting macroporous co-polymer is then isolated by conventional means, such as de-watering or evaporation, followed by drying.

Suitable porogens for use in the present invention are liquids meeting the following criteria: (i) they are either fully miscible with the monomer mixture or capable of being made fully miscible by the addition of a minor amount of non-water-miscible solvent; (ii) they are immiscible with water, or at most only slightly soluble; or (iii) they are inert with respect to the monomers, and stable when in contact with any polymerization catalyst used and when subjected to any conditions needed to induce polymerization (such as temperature and radiation); and (iv) they are normally liquids or have melting points below the polymerization temperature. Solids can frequently be converted to liquid form by being dissolved in a solvent or by forming eutectic mixtures. See e.g., U.S. Pat. No. 6,323,249 as an example of another type of porogen that is polymeric.

Preferred porogens for use in preferred embodiments of the invention include, but are not limited to, water or hydrocarbons, particularly inert, nonpolar organic solvents. Some of the most convenient examples are alkanes, cycloalkanes, and aromatics. Examples of such solvents are alkanes of 5 to 12 carbon atoms, straight or branched chain, cycloalkanes of 5 to 8 carbon atoms, benzene, and alkyl-substituted benzenes. Preferred porogens comprise xylene, toluene, acetates, such as butyl acetate, isobutyl acetate, alcohols, and plasticizers, such as adipates and phthalates.

After formation of the porous beads, the beads are separated from the phase and subjected to one or more purification steps, such as washing, to remove any unreacted monomer or impurity from the beads. However, the purification of the beads does not necessarily require removal of the porogen from the network of pores within each of the beads. After purification, the beads may be dried (e.g., by spray drying) by conventional operation to obtain a powder-like substance comprising the beads which have retained the porogen within the network of pores to serve as an active ingredient when the beads are used as a controlled-release delivery vehicle. In a preferred embodiment the thus-produced dry beads or microspheres are ground to reduce the size of the polymer aggregates and also reduce the ratio of macropores in the mass, further controlling the ability to control release of the active ingredient contained therein.

In an alternative preferred method, the porogen is completely removed by solvent extraction (e.g., using isopropanol), evaporation, drying, or similar operations and then replaced (e.g., by contact absorption) with the active ingredient in a two-step process of the type disclosed in U.S. Pat. No. 5,955,109 (herein incorporated by reference). Once washing of the polymerized beads or microspheres is complete, the solvent itself is removed by drying, preferably in a vacuum.

In certain cases, another alternative method of extraction may be used, i.e., where the porogen, unreacted monomer and water will form an azeotrope. In these cases, steam distillation is an effective way of extracting porogen from the beads. This may also be followed by drying under vacuum.

The drying or porogen removal step also advantageously eliminates unwanted materials, such as unreacted monomers, residual catalyst or initiator compounds, and surface active agents (e.g., surfactants) or dispersants remaining on the microsphere surfaces, from the polymerized particles and network prior to incorporation of the active ingredient. It also permits greater control over the characteristics of the finished bead and the quantity of active ingredient. In yet another alternative, because the active ingredient is added into the pores of preformed dry porous polymer beads, commercially available beads of suitable pore structure could be used, although such beads would offer less controlled release of the active ingredient because the active ingredient could only be incorporated into the pore network, not into the particles.

In the alternative two-step method, the most convenient method for impregnating the pore network with the active ingredient, is contact absorption. The selected active ingredient is first dissolved in a solvent, and the resulting solution is absorbed by the beads. The solvent may either be retained in the finished product or removed by conventional means such as evaporation or extraction using a secondary solvent. Since certain active ingredients will have limited solubility in most solvents, the absorption process is repeated as often as needed, each repetition followed by solvent removal until the desired high concentration is reached in the finished bead. Usually, the absorption/evaporation cycle will be repeated at least once, usually twice, and frequently three or more times, in order to obtain final concentrations of 1%, or higher.

Suitable organic solvents for decreasing viscosity and facilitating absorption of the active ingredient include, for example, liquid petrolatum, ether, petroleum ether, alcohols including methanol, ethanol and higher alcohols, aromatics including benzene and toluene, alkanes including pentane, hexane and heptane, ketones including acetone and methyl ethyl ketone, chlorinated hydrocarbons including chloroform, carbon tetrachloride, methylene chloride and ethylene dichloride, acetates including ethyl acetate, and oils including isopropyl myristate, diisopropyl adipate and mineral oil. A preferred solvent for this purpose is acetone or isopropanol, where solutions of up to <1% to 20%, more preferably 1% to 10%, even more preferably 1% to 5% and most preferably 1% to 2% by weight of the active ingredient can be obtained.

Other formulating materials, such as carriers or adjuvants such as fragrances, preservatives, antioxidants, and other emollients can also be present, and will be incorporated into and onto the beads together with the impregnated active ingredient and any other materials present.

In their most convenient form, the particles are generally spherical in shape, as a result of the use of suspension polymerization as a preferred method of preparation. While the microspheres may vary widely in size, those falling within the range of about 0.10 microns to about 100 microns in diameter, preferably from about 1.0 to about 70 microns, more preferably from about 10 to about 40 microns will provide the best results. Microspheres within these size ranges are appealing from an aesthetic point of view by imparting a smooth feel to the touch and a smooth coat.

The pore dimensions within the spheres may also vary widely, with optimum dimensions depending on the chemical characteristics of the polymers used, as well as the diffusive characteristics of the active ingredient. Different delivery systems will thus require different optimum ranges of pore volume distribution to obtain the most desirable properties for the overall formulation. In general, however, the best delivery results are obtained with total pore volumes ranging from about 0.01 to about 4.0 cc/g, preferably from about 0.1 cc/g to about 2.0 cc/g. Surface areas range from about 1 to about 1000 m$^2$/g, preferably from about 10 to about 600 m$^2$/g, more preferably from about 20 m$^2$/g to about 300 m$^2$/g. Average pore diameters range from about <20 Å to 10,000 Å, preferably from 0.001 micron to about 3.0 microns, more preferably from about 0.003 to about 1.0 microns.

Following the use of conventional methods for measuring and expressing pore sizes, the pore diameters are calculated from the measurement of the surface area by B.E.T. nitrogen multipoint analysis (Brunauer, Emmett, Teller, *Am. Chem. Soc.* 60:309-316 (1938)) and from the measurement of the pore volumes by the mercury intrusion method. The nitrogen adsorption isotherm method is described in detail in (Barrett et al., *J. Am. Chem. Soc.*, 73:373-80 (1951)).

Such calculations are commonly performed by those skilled in the art. Based upon the ratio of nitrogen adsorption/desorption in terms of the quantity of pores, the resulting graphs show the ratio of macropores (wherein ingress or egress is rapid) as compared with micropores (wherein the channels are so small as to be controlled by capillary action forces and egress is very, very slow).

The process of the present invention can be designed to control porosity and the particle diameter of the beads, which are substantially spherical. Under identical polymerization conditions, the porosity can be increased by increasing the calculated or theoretical cross-linking density or by increasing the porogen concentration in the solution. An increase in porosity will increase the surface area of the bead. Thus, the weight percent of the porogen which can be held within the bead is also directly increased.

The gel phase can be fully crosslinked, but it is preferred to have a portion of the polymeric gel phase (less than 15%) crosslinked enabling effective gel phase diffusion of the active material to be delivered. Typically the largest pores in the gel phase range from approximately 30 to 42 angstroms in diameter and will permit effective diffusion of molecules if they are less than 2000 daltons.

To decrease the particle diameter under identical polymerization conditions, the agitation and/or the concentration of dispersion agents in the phase are increased. By controlling the porosity and the particle diameter of the bead, a delivery vehicle suitable for use in the method of the present invention is obtained. Generally speaking, it has been found that it is preferable for the bead to have a diameter from about 0.10 microns to about 1000 microns, more preferably from about 1.0 microns to about 500 microns, and more preferably from about 5 microns to about 100 microns, and to have a calculated cross-linking in excess of about 10%.

Although trace amounts may be used, the active ingredient typically comprises between approximately 1% to approximately 90%, more often 5% to approximately 60% of the total weight of the composition or delivery vehicle comprising the polymeric bead and the active ingredient of the preferred embodiments of the present invention.

To distinguish whether a composition possesses sufficient mechanical strength to be used as a delivery vehicle for providing controlled time-release of the active ingredient, the composition can be subjected to a wetting test. If the composition has a calculated cross-linking density and an active ingredient concentration, such that substantially all of the active ingredient will be released from the network of pores when the bead is placed in a solvent in which the active ingredient is soluble, for a sufficient length of time to wet the bead, then the composition can be used in the method of the present invention.

A wetting test can be performed by weighing a dry sample of material to be tested containing an original amount of active ingredient. The dry sample is then mixed with a solvent in which the active ingredient is soluble to form a wet sample. The wet sample is then agitated for a sufficient length of time to wet the bead if the dry sample comprises a delivery vehicle according to the present invention. The amount of active ingredient released into the solvent is then determined. The amount of active ingredient released into the solvent will be substantially the same as the original amount of active ingredient if the dry sample consisted essentially of the delivery vehicle whereas the released amount will be substantially less than the original amount if the dry sample contained a substantial amount of a gel product or a microencapsulated product.

The polymerization process and the various parameters and process conditions involved in the polymerization can be selected and adjusted as a means of controlling the pore characteristics and consequently the capacity and release characteristics of the ultimate product. For example, proper selection of the cross-linking means, the amount and type of cross-linking agent, and the amount and type of porogen are means of attaining such control. Cross-linking or interlinking of the polymer networks or channels is a well-documented principle involved in encapsulated polymer compositions. Certain polymerization conditions may also be varied to such effect, including temperature, degree of radiation (if used), degree of agitation and any other factors affecting the rate of the polymerization reaction.

Cross-linking in the polymer formation is a primary means of controlling pore size. Monomers, which may be polymerized to produce cross-linked polymer beads in accordance with the present invention, include polyethylenically unsaturated monomers, i.e., those having at least two sites of unsaturation, and monoethylenically unsaturated monomers in combination with one or more polyethylenically unsaturated monomers. In the latter case, the percentage of cross-linking may be controlled by balancing the relative amounts of monoethylenically unsaturated monomer and polyethylenically unsaturated monomer. The polymer beads of the present invention will have greater than 10% cross-linking, preferably from about 10% to about 80% cross-linking, and most preferably from about 20% to about 60% cross-linking.

The "percentage cross-linking" is defined by those skilled in the art as the weight of polyethylenically unsaturated monomer or monomers divided by the total weight of monomer, including both polyethylenically unsaturated and monoethylenically unsaturated monomers.

The process of the present invention can be conducted without using expensive and environmentally toxic solvents, such as chloroform or other chlorinated solvents, which are often used in interfacial polymerization. Further, since it is desired to leave the porogen held within the network of pores, there is no need for an additional washing step in which the porogen must be dissolved to be removed from the network of pores. Accordingly, the process of the present invention can be very economical with a minimal exposure of possible environmental pollution when a suitable activator and phase or solvent are selected.

Monoethylenically unsaturated monomers suitable for preparing polymer beads for the polymer delivery system include ethylene, propylene, isobutylene, diisobutylene, styrene, ethylvinylbenzene, vinylpyridine, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl ketone, vinyl isopropyl ketone, and methyl isopropenyl ketone; vinyl ethers, including vinyl methyl ether, vinyl ethyl ether, vinyl propyl ether, hydroxyethyl (meth)acrylate, hydroxypropyl (meth)acrylate; aromatic vinyl compounds, such as styrene; substituted styrenes; butadiene; acrylonitrile; monomers containing acetoacetoxy functional groups, such as acetoacetoxyethyl methacrylate; vinyl acetate; acid or base containing monomers, such as, for example, (meth)acrylic acid, itaconic acid, maleic acid, fumaric acid, N,N-dimethylaminoethyl methacrylate; or combinations thereof. Additionally, cross-linking and grafting monomers, such as 1,4-butyleneglycol methacrylate, trimethylolpropane triacrylate and trimethacrylate, allyl methacrylate, diallyl phthalate, divinyl benzene, or combinations thereof may be used. As used herein, by "(meth)acrylate" or "(meth)acrylic" is meant either acrylate or methacrylate for "(meth)acrylate" and acrylic or methacrylic for "(meth)acrylic." Also applicable are glycerol methacrylate and glycerol dimethacrylate, as a well as other specialty monomers and crosslinkers, sold by companies, such as Rohm America (Piscataway, N.J.), Sartomer (Exton, Pa.), Dow Chemicals (Midland, Mich.), Elf Atochem (Philadelphia, Pa.), and Monomer Polymer & Dajac Laboratories (Zurich, Switzerland).

Polyethylenically unsaturated monomers, which ordinarily act as though they have only one unsaturated group, such as isopropene, butadiene and chloroprene, may also be used as part of the monoethylenically unsaturated monomer content.

Polyethylenically unsaturated cross-linking monomers suitable for preparing such polymer beads, include diallyl phthalate, ethylene glycol diacrylate, ethylene glycol dimethacrylate, trimethylolpropanetri-methacrylate, divinylsulfone; polyvinyl and polyallyl ethers of ethylene glycol, of glycerol, of pentaerythritol, of diethyleneglycol, of monothio- and dithio-derivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene, alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

The preferred polymer bead of the present invention is free from reactive groups which will cause unintended interactions with the porogen and the active ingredient which is ultimately incorporated in the composition. Thus, the selected beads are stable over a wide pH range, resist moderate oxidation and reduction, are stable at higher temperatures, resist attack by moisture, and have a relatively long shelf life.

Particularly preferred polymer delivery systems of the present invention are formed by the co-polymerization of styrene and divinylbenzene, vinyl stearate and divinylbenzene, 4-vinylpyridine and ethylene glycol dimethacrylate, or methylmethacrylate and ethylene glycol dimethacrylate or trimethylol propane trimethacylate. Typically, the monoethylenically unsaturated monomer will be present at from about 10% to 98%, more often from 20% to 80% of the monomer mixture, with the polyethylenically unsaturated monomer forming the remainder of the mixture. Particularly preferred in the present invention is a styrene-divinylbenzene polymeric bead, which consists essentially of a hydrocarbon backbone with benzene rings, and which is essentially completely free from reactive groups, as well as beads made from acrylic cross-linkers, such as ethylene glycol dimethacrylate and trimethylol propane trimethacrylate.

Utility of the Present Invention as a Nail Coating Film

In a preferred embodiment of the present invention, the "coating composition" is intended for use on nails, specifically the nail surfaces of the fingers and toes, for such purposes as changing the cosmetic appearance of nails, strengthening nails and hardening nails. For example, the nail coating composition can be a nail polish, nail lacquer, nail enamel, top coat, base coat, nail strengthener, nail hardeners, nail polish quick dry product, as well as cyanoacrylate glue adhesives and coatings, acrylic monomer and polymer artificial nail systems, in addition to gels such as urethane acrylate ultraviolet-cured coatings.

A preferred embodiment of the present invention provides an integral, self-contained nail enamel/nail enamel plasticizing agent. Minute, plasticizer-containing beads are preferable, which are homogeneously dispersed within the nail polish. In practical use, the nail polish is applied to the nail surface in known manner and allowed to air-dry and harden. In an alternative preferred embodiment, the coating composition further comprises a UV-activated initiator, and the coating is then cured by timed exposure to UV light.

In either case, the nail polish may be thereafter removed whenever desired by any known means, e.g., by simply wiping the nail polish off with a cosmetic cotton or tissue comprising any one of the many commercially available, recognized solvents for dissolving the dried nail enamel. While personal use by humans is preferred, uses on animals, plants, and the like, are not excluded.

For the nail lacquers, the film forming process involves two steps following liquid application. First, most of the solvents in the system evaporate (flash) to form a hardened film coating at the air interface. The rate of this development is dependent upon the balance between the solvents and the percentage of plasticizers used. The second step is more critical because the rate of evaporation of the remaining solvents must be controlled at a sufficiently slow rate to maintain an invisible flow in the film—'the internal flow.' It is this internal flow that helps to keep the constituents beneath the hard film exterior surface soft and pliable, and permits the coating to absorb impact force at a level that would otherwise directly or indirectly cause the film to chip or crack. Nail enamel can be formulated to reach its optimal hardness over a period of 24-48 hours, but once the optimal point has been reached, the coating maintains that level for 5-10 days. Thus, the effect of the internal flow is preserved and maintained for at least 5 days, and extending to 10 days or more, before film degeneration occurs, primarily because of the effect of the plasticizers present in the composition.

Therefore, the invention advantageously provides a liquid nail coating composition, which when dried, has improved durability, combined with resistance to chemicals and abrasion, while remaining removable upon application of commercial nail solvents. The choice of possible formulations for the subject coating compositions, is constrained and delimited by, among others, the following requirements: (i) compatibility, both physical and chemical, with customary nail polish formulants and pre-cursor materials, which can include both hydrophilic and lipophilic materials; (ii) stability (physical, chemical and biological) of the end-product formulations for extended distribution and shelf-life, especially against settling, loss of volume and spoilage; (iii) end-product stability for the consumer after opening; (iv) end-use functionality which, in addition to ornamental or protective functions, includes the more elusive qualities of feel and ease of application, as well as durability and adhesion; and (v) safety, e.g., non-toxicity, non-comedogenicity, hypoallergenicity and the like, to the wearer.

An "aqueous" nail coating composition contains at least 35 weight percent, preferably from 45 weight percent to 90 weight percent, and most preferably from 45 weight percent to 55 weight percent of water.

To utilize a delivery vehicle in accordance with the method of the present invention, the delivery vehicle is mixed with a medium to form a system, which is applied to the nail surface. The active ingredient is then released from three unique, but interrelated, routes by a force or energy: (i) the gel particle porosity, (ii) the network of macropores, (iii) the network of mesopores, and (iv) the network of micropores. The controlled time release occurs through diffusion, osmosis, or volatization, each of which is attributable to changes in kinetic energy, or by some combination thereof. Alternatively, the active ingredient may be released by a force, such as pressure, although pressure generated release may by gradual and continuous. Pressure release may also be triggered by intermittent pressure, which may vary the concentration of active ingredient released from the network of pores, and its rate of discharge.

A delivery vehicle of the present invention is mechanically strong because of the polymeric structure of the bead and the degree of cross-linking or co-polymerization. It is believed that the bead can be conceptualized as a rigid sponge, i.e., a structural network formed by three dimensional cross-linking or co-polymerization, which leaves random spaces or holes which collectively form the network of pores. The polymeric structure or bead physically holds the active ingredient in the network of pores because the active ingredient diffuses into the polymeric structural network being formed during polymerization of the bead. It is then held or trapped until an external force or energy releases the porogen from the particles and network of pores in the polymerized bead. However, unlike a gel in which the polymeric structural network collapses when the material held within said network is removed or released, a delivery vehicle according to the present invention possesses a certain minimum degree of calculated cross-linking density for a given active ingredient concentration, causing the entire structure or bead to have sufficient strength to prevent substantial shrinking or collapse of the bead when the porogen is removed from the network of pores.

Plasticizers as an Active Ingredient

Nail enamels must be durable to resist physical and harsh household chemical attack and must also be flexible since the human nail is pliable and grows with time. Hence, to improve the tensile strength and adhesion characteristics of nail enamels, plasticizers and resins have generally been added to the typical nitrocellulose film forming composition.

Dibutyl phthalate (DBP) has been used as the plasticizer of choice for many years since it provides excellent flexibility, elongation and tensile strength to nail polish formulations. DBP is the aromatic diester of butyl alcohol and phthalic acid, resulting in an aromatic structure. Alkyl adipates are the esters of alkylalcohols and adipic acid, resulting in a linear chain structure. Because alkyl adipates are less electron repelling, it is easier for film constituents to attach, resulting in a stronger bond with the constituents than with DBP.

Preferably, the compositions of the present invention comprise conventional ingredients: i.e., nitrocellulose as a primary film forming agent, acrylate co-polymers may be added as a secondary film forming agent; ketones such as methyl ethyl ketone, isopropyl alcohol, diacetone, ethyl or butyl acetate as solvents and optionally, toluene as a solvent, phthalic anhydride/trimellitic anhydride/glycol co-polymers and tosylamide formaldehyde resins as adhesion promoters and any one or more of a countless number of FD & C colorants useful as colors for the composition. The plasticizer, which gives the superior performance to the coating when released as an active ingredient in the delivery system of the present invention, is selected from the group including: DBP or phthalates; an adipate; pentaerythrityl tetrabenzoate; or 2,2,4-trimethyl-1,3-pentanediol diisobutyrate, and the like, or combinations thereof.

In a preferred embodiment, DBP is the plasticizer of choice, and DBP is incorporated in the nail enamel formulations of the preferred embodiment in amounts of from 0.1 to 15.0 weight percent (wt %) based on the total weight of the enamel composition. When dioctyl adipate is the plasticizer of choice in the present invention, (bis)2-ethylhexyl adipate (referred to as DOA) may be used. 2,2,4-trimethyl-1,3-pentanediol diisobutyrate (TXIB) is another plasticizer that is extremely effective in producing nail enamels that are both flexible durable and long lasting. Pentaerythrityl tetrabenzoate is yet another preferred plasticizer, wherein the R group is preferably a benzyl. Thus, the plasticizer may also act as an adhesion promoter and flow aid. A number of other adipates and pentaerythrityl tetraacetates may be substituted therefore, such as diisobutyl adipate, dipropyl adipate, diisostearyl adipate, diisocetyl adipate, diisodecyl adipate, diisononyl adipate, or pentaerythrityl tetraacetate (each at 0.1-15.0 wt %). Moreover, combinations of two or more plasticizers are found in alternative embodiments of the nail coatings of the present invention.

The remaining ingredients in the novel nail coating formulations of the present invention include those compounds well known in the nail polish industry. A film-forming agent is preferred in order to provide the nail enamel with a consistency that results in the formulation of a uniform, stable film on the surface of the nail when the enamel is applied thereon. Nitrocellulose is the preferred film-former incorporated in the formulation in amounts that will cause the enamel to readily spread over the surface of the nail, yet remain viscous enough to not run or drip. However, it must also readily cling to and flow from the applicator brush as the enamel is applied from bottle to nail, and thus it generally comprises from about 5.0 to 40 wt % of the total weight of the composition, and preferably will be incorporated in amounts of from about 3 to about 30 wt %. Other suitable, although not necessarily preferred film formers include: cellulose acetate butyrate, polyurethanes, and mixtures thereof.

The solvent components are selected to be as inert to the user's nail and to the other components of the nail enamel composition as possible. The solvent should also be capable of dissolving or dispersing the other components so that they readily flow onto the nail. The solvent must be able to evaporate from the nail in a matter of minutes at room temperature and pressure so that the film forming agents, plasticizers and other components dissolved therein solidify and adhere to the nail surface. Examples of preferred solvents include: isopropanol, butyl acetate, ethyl acetate, propyl acetate, and mixtures thereof. Effective amounts of the solvent component will generally lie in the range of about 30 wt % to about 70 wt % of the composition.

A suspending agent is an optional, but preferred, component of the nail enamel compositions of the present invention. The suspending agent should help suspend the pigments in the nail enamel, and helps adjust the viscosity of the enamel to achieve desired flowability. Examples of preferred suspending agents include: montmorillonite clays, and treated clays such as stearalkonium hectorite, which are preferred. The amount of the suspending agent depends on the desired flow characteristics of the nail coating, but amounts on the order of about 0.2 to about 2.0 wt % are generally satisfactory.

The nail enamel compositions of the present invention can be clear, i.e., unpigmented, or they can include a pigment component. The term "pigment" includes mixtures of compounds well known in the nail coating industry. See, e.g., U.S. Pat. Nos. 5,133,966; 4,832,944; and 5,174,996. The amounts of any particular ingredients comprising the pigment component will, of course, depend on the shade desired or needs of the practitioner. In general, the pigment component comprises about 0.01 to about 15.0 wt % of the composition.

Nail enamels in accordance with the present invention are manufactured by thoroughly and intimately mixing together at least all of the components indicated above, in the amounts described above, using methods and equipment known to those of ordinary skill in the nail coating art when plasticizers are added. As a result, the nail coating formulation of the present invention, when a preferred plasticizer is the active ingredient provides a superior long-lasting color and gloss that is chip resistant, durable, flexible and will withstand harsh household chemicals, adverse temperatures and the effects of other external factors for long periods of time.

Vitamins as an Active Ingredient

In an embodiment of the invention, vitamins are added as an essential active ingredient to be delivered from the delivery vehicle. Vitamins are chemically unrelated, fairly complex organic substances that are essential in small amounts for the maintenance of normal metabolic functions. Vitamins are not synthesized within the human body, and must therefore be furnished from exogenous sources. Natural sources of vitamins include plant and animal tissue.

Vitamins can be broadly categorized as either fat-soluble or water-soluble. Vitamins A, D, E and K are fat soluble and are absorbed in association with lipids. Vitamins $B_1$, $B_2$, $B_5$, $B_{12}$, $B_{15}$, $B_{17}$, C, niacin, folic acid, pantothenic acid, biotin, bioflavonoids, choline, inositol and F are examples of water-soluble vitamins. Vitamins A, D and E, and derivatives thereof, including esters, such as vitamin A palmitate, vitamin E acetate, and vitamin E palmitate, and substances which contain such vitamins and vitamin derivatives, such as fish oils, have long been known to be useful for various topical therapeutic and cosmetic purposes.

Creams, ointments and powders containing vitamins A and D as such or cod liver oil have been used for the prevention and treatment of prickly heat and diaper rash in infants. Vitamin E and vitamin E esters, such as the acetate and palmitate, have been used, typically in creams, ointments, lotions, oils and other cosmetic formulations, as skin moisturizers and smoothers, to treat chronic skin diseases, to aid in healing burns and wounds, to reduce scarring from wounds, as topical anti-inflammatory agents, and to protect the skin from damage from ultraviolet rays. Vitamins or botanicals may require the presence of acid or base groups to permit ionic bonding to occur.

Delivery of Other Active Ingredients

In yet another embodiment, other active ingredients are added for delivery from the delivery vehicle. By "active ingredient" is meant a substance less than approximately 2000 daltons that will benefit the substrate or the coating composition in which the material is placed. Examples of other active ingredients that may benefit the coating material and or substrate (in addition to the preferred plasticizers, vitamins and botanicals) include, but are not limited to, pigments, dyes, stabilizing agents such as UV absorbers (such as, 2-hydroxy-4-methoxy-benzophenone) and blockers, brighteners, fragrances, flavors, opacifiers, oils, moisturizers, antioxidants, solvents, bactericides, mildewcides, fungicides, herbicides, pesticides, stabilizing agents, such as inhibitors and or radical traps, antibiotics, antimicrobials, slip agents, catalysts, and the like. It is also contemplated that the invention can be used for delivery of or stabilizing antibiotics, antimicrobials, topical therapeutic drugs, radiation treatment and imaging materials. However, as presently described, the present delivery system and methods are not intended for internal or ingested pharmaceutical, therapeutic or diagnostic applications.

Additional objects, advantages and novel features of the invention will be set forth in part in the description and examples and figures which follow, and in part will become apparent to those skilled in the art on examination of the following, or may be learned by practice of the invention. The following examples, however, are understood to be illustrative only and are not to be construed as limiting the scope of the appended claims. Unless otherwise indicated, the amounts of the ingredients in the following examples refer to parts by weight.

EXAMPLES

Example 1

Controlled, Sustained Slow Release of an Active Ingredient

Experiments were conducted to determine the effectiveness of the pore network for the controlled, sustained slow release of an active ingredient from a film coating. The tests showed that the large pores (macropores) release small molecules too fast to contribute to the sustained release aspect of the present invention. By comparison, when porosity is high, in the less than 20 to 250 Å range, as disclosed in the micropores and mesopores of the present delivery vehicle, the release of the desired active ingredient to the substrate takes place over a much longer time period. For instance, in one sample, naphthalene has been steadily released for 6 weeks. In another, DBP has been released for over three weeks.

Moreover, the delivery can be modified by changing the pore size and it's distribution, porosity, surface area, as well as the polymeric material make up. For example, the release of dibutyl phthalate is much slower from an aromatic polymer backbone as opposed to from an acrylic backbone. So if a longer release time is needed an aromatic composition is used, whereas if a shorter more concentrated delivery is desirable, an acrylic polymer can be used. Apparently the acrylic bead has much better mass transfer and diffusional characteristics when using dibutyl phthalate as the active molecule being delivered.

The concept has been tested on cellulosic films, and acrylic molded articles, such as polyethyl methacrylate and polymethyl methacrylate. Particularly preferred polymer delivery systems of the present invention are formed by the co-polymerization of styrene and divinylbenzene, vinyl stearate and divinylbenzene, 4-vinylpyridine and ethylene glycol dimethacrylate, or methylmethacrylate and ethylene glycol dimethacrylate. Usually, the monoethylenically unsaturated monomer is present at from about 20% to 80% of the monomer mixture, with the polyethylenically unsaturated monomer forming the remainder of the mixture. Particularly preferred is the styrene-divinylbenzene polymeric bead which consists essentially of a hydrocarbon backbone with benzene rings, and which is substantially completely free from reactive groups.

The surface area of several samples of the purified beads was determined by the B.E.T. method to range from 5 m$^2$/g while the pore volume was determined by nitrogen adsorption isotherm to be 0.1028 ml/g to 1200 m$^2$/g.

Delivery of calcium pantothenate ($C_9H_{17}NO_5 \cdot \frac{1}{2}Ca$) over time is shown in FIG. 1. Calcium pantothenate is structurally much like DBP, although not an aromatic. The immediate release from the macropores is apparent in the first day or two, while the sustained slow release from the remainder of the pore network and the gel continues at least through day 15.

Figure 2:
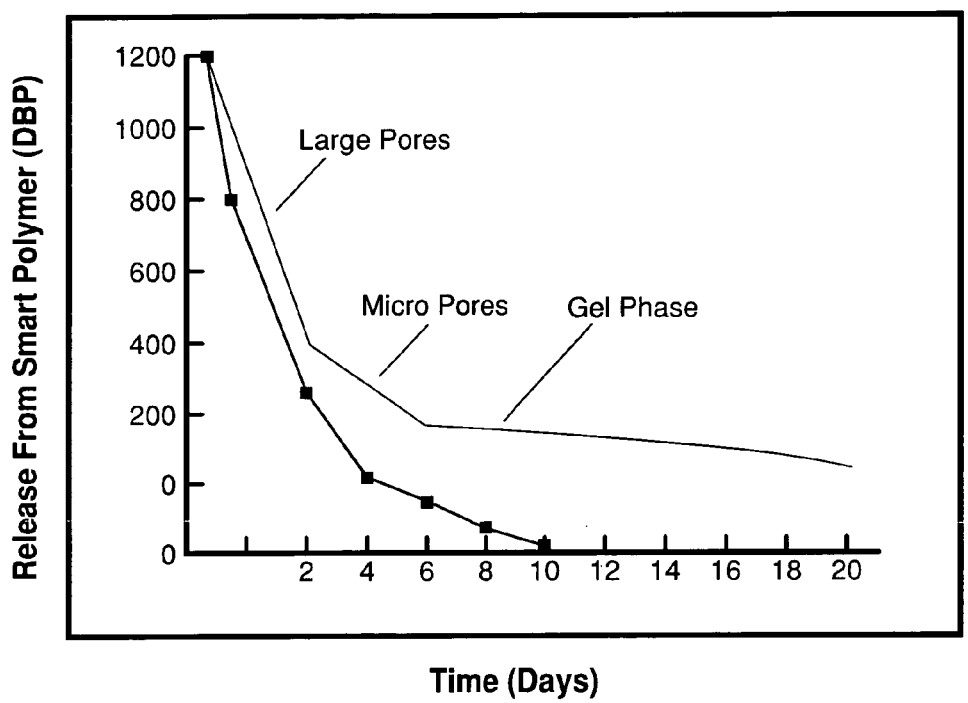
FIG. 2 graphically shows the controlled release delivery of an aromatic compound, dibutyl phthalate (DBP), over a time course of 20 days. Immediate release from the macropores drops is apparent in the first day or two, while the sustained slow release from the remainder of the pore network and the gel continues at least through day 15.

By comparison, delivery of the aromatic composition, dibutyl phthalate (DBP), over time is shown in FIG. 2. Again the immediate release from the macropores is apparent in the first day or two, while the sustained slow release from the remainder of the pore network continues at least through day 20. The release on days 6 through 20 approached an optimal steady state.

Example 2

Effect of Adding Present Delivery Vehicle to Gel or Coating Compositions Over Time In styrene or acrylic nail coatings, dibutyl phthalate (DBP) is a plasticizer of choice. Consequently, a delivery system and method providing for the long term, continuous controlled release of DBP into the dried coating maintained an internal flow within the physical structure of the coating, thereby significantly enhancing durability, while providing novel resistance to cracking, chipping, or brittleness. The following gels and coatings were prepared to which the delivery vehicle was added as shown in Table 1.

Clear Base A (gel) was generated as follows: to a 600 ml beaker, 0.25 g Irganox 184, 0.5 g Irganox 625, 0.25 g BPO, 20 g PEG-monomethacrylate, 20 g furfuryl-methacrylate, 5 g DBP, 20 g of RX01336 di-urethane acrylate, and 5 g of PEG-tri-acrylate are added. The mixture was stirred at room temperature until a clear, solution was obtained.

Clear Base B (coating) was generated as follows: to a 600 ml beaker, 120 g IPA, 914 g ethyl acetate, 341 g n-butyl acetate, 324 g nitrocellulose, 162 g polyester resin, 308 g polyacrylic resin, 30 g alkyl citrate, 28 g camphor, and 5 g etocrylene are added. The mixture was stirred at room temperature until a clear, pale yellow solution was obtained.

Clear Base C (gel) was generated as follows: to a 200 ml beaker, 0.6 g BPO, 4.6 g hydroxy-acrylate, 70.0 g diurethane acrylate, 20.0 g triacrylate ester, and 7.5 g silica is added. The mixture was stirred at room temperature until a clear, solution was obtained.

Clear Base D (coating) was generated as follows: to a 600 ml beaker, 581 g ethyl acetate, 903 g n-butyl acetate, 271 g IPA, 887 g nitrocellulose, 271 g polyester resin, 90 g alkyl phthalate, 90 g camphor, 6.0 g UV Inhibitor, and 3 g Flow Aid is added. The mixture was stirred at room temperature until a clear, pale yellow solution was obtained.

Paste A was generated as follows: to a 600 ml glass beaker, 10.9 g poly(DVB)-co-(EVB) absorbent gel with an average particle size of 25 micron, 1.9 g polyacrylate fluid aid, 56.3 g polyester resin, and 21.3 g DBP. The mixture was homogenized using a Cowles type dispersing mixer for 30 minutes, resulting in a thick paste having an average particle size of <30 microns, as indicated by a grind gauge apparatus. This paste, essentially acting as a plasticizer, was then added without dilution to various solvent-based, low solids formulations as shown in Table 1. The gel and the coating were specifically selected as materials that were known to exhibit poor adhesion to the nail for ease in determining appearance in terms of adherence within the allotted time period.

TABLE 1

Slow release of active ingredient results in long term durability of both coatings and gels.

|  | Gel 0 | Gel 1 | Gel 2 | Coating 0 | Coating 1 | Coating 2 |
|---|---|---|---|---|---|---|
| % | 100% | 99% | 90% | 100% | 99% | 90% |
| Paste A | 0% | 1% | 10% | 0% | 1% | 10% |
| Appearance | lifting | lifting | lifting | free edge chipping | free edge chipping | free edge chipping |
| Day 1 | 10 | 10 | 10 | 10 | 10 | 10 |
| Day 5 | 6 | 7 | 7 | 5 | 4 | 8 |
| Day 10 | 3 | 2 | 7 | 2 | 2 | 7 |
| Day 15 | 1 | 0 | 6 | 0 | 2 | 4 |
| Average score | 5 | 4.75 | 4.5 | 4.25 | 4.5 | 7.25 |

Score of 10 = perfect;
score of 0 = poor.

In each case, whether charged with 1% paste:99% gel or coating, or charged 10% paste:90% gel or coating, the samples were prepared by mixing in a Cowles type dispersing mixer for 30 minutes. The resultant fluid was in each case allowed to stand overnight before being applied to a nail surface to test for appearance as shown in Table 1.

The advantages of adding Paste A, which represented the slow release vehicle of the present invention, are clearly seen by the enhanced durability shown when the nitrocellulose coatings or the gels were applied to a nail. The pure gel or coating preparations, indicated by "0" represent a base line preparation, without the enhancing durability of the present invention. All looked "perfect" with a score of "10" on Day 1, and the pure preparation without Paste A all had deteriorated to very poor, with a score of "0" to "1" on Day 15. When only 1% of Paste A was added, the change from the pure preparation was essentially the same on Day 5, Day 10 and Day 15. However, when 10% of Paste A was added, the benefits can be readily seen in both the durable appearance of both the gel and the coating. At Day 15, the appearance score improved in the gel to a value of "6", as opposed to only "1" in the pure gel; the score in the coating was "4" as opposed to "0" in the pure coating—essentially a increase by at least 40 to 60% in durability, as evaluated in terms of appearance in this example, achieved simply by the addition of only 10% Paste A.

Example 3

An Exemplary Method for Applying the Durable, Slow Releasing Material as a Nail Coating The following provides a description of a method of actually using the durable, slow releasing coating of the present invention as a nail coating using an innovative Premium Gel that provides a base, builder and top gel, all in one—the One Phase System for nails. The only difference between this preparation and that which is described above, is that this preparation further adds the element of UV curing, which is not required in the air-dried preparations described above. However, the net effect is essentially the same, and it provides the steps by which the durable coating of the present invention can actually be applied to a surface, in this case human finger nails. Thus, a system for nail coating is provided. The system is best applied to a freshly-cleaned nail surface.

The applied composition is an acrylic monomer preparation and urethane acrylate oligomers, combined with a UV-activated initiator. No primer is required because the gel itself has adhesive properties. The gel comprising the durable, slow release composition of this invention, was placed (enough to build a thick layer) in the center of the nail, at the point of the c-curve. Working in very small circular motions, the gel was moved towards the cuticle, creating a very thin layer along the cuticle area. Working outward, more gel was left in the center of the nail, and tapered off towards the end of the nail, where the gel became very thin.

The finish is then cured for 3 minutes with a UV light device (e.g., Eurolight; Keystone Industries, Cherry Hill, N.J.), followed by curing for 1½ minute under a 7/9-watt incandescent light. Then a selected second decorative or protective layer, such as a nail polish or lacquer comprising the durable, slow release gel coat, is applied very smoothly, but not too thin. This reduces filing. The finish is again cured for 3 minutes with a UV light device (Eurolight), followed by curing for 1½ minute under a 7/9-watt incandescent light. It was found that it was important to always use the maximum time for curing to permit complete curing of the gel coat. If it is not completely cured, the surface tends to lift within a day. Moreover, no cleansing step is permitted between the two layers of gel.

After the completion of the second of the curing steps, the nails are cleansed. In fact, after curing of both gel layers is completed (after the second series of curing steps), a sticky residue will remain, which is removed by recognized cleaning methods, e.g., the Eurocleanser (Keystone Industries, Cherry Hill, N.J.). The gel will stay tacky until it is cleansed. This is not because the gel did not cure completely. Rather, it is because the gel is not under vacuum while curing. Vacuum curing would eliminate the stickiness, but is impractical for normal commercial purposes. Once, free of the stickiness, the gels can be filed and contoured.

After curing and cleaning the nails can be filed as usual, preferably thin at the cuticle area and end of nail and broader at the breakpoint. One or two millimeters should be filed off of the ends of the treated nail, since gels can shrink up to 3%-5%. These gels are made and have the same strength as acrylics, but they can be applied very thin, giving the nails a very natural look. Advantageously, however, as proven in Example 2, the "perfect" look achieved by this coating process will maintain an acceptable appearance for much longer (at least 40% to 60% longer) than comparable prior art preparations, including acrylic preparations. Moreover, the slow release capability of the preparation permits the addition of additional active materials, such as plasticizers, pigments, dyes, stabilizing agents such as UV absorbers and blockers, brighteners, fragrances, flavors, opacifiers, oils, moisturizers, antioxidants, solvents, bactericides, mildewcides, fungicides, herbicides, pesticides, vitamins, stabilizing agents such as inhibitors and or radical traps, antibiotics, antimicrobials, slip agents, and catalysts, and the like, or for the delivery of stabilizing antibiotics, antimicrobials, therapeutic drugs, radiation treatment and imaging materials, and the like. The coating process also provides a flexible, non-brittle composition that resists chipping or pealing, even in adverse conditions.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method for sustained delivery of an active ingredient into a film coating and sustained delivery therefrom, comprising the steps of:

preparing a mixture, comprising at least one active ingredient and a population of stable, homogeneously-dispersed, porous polymeric or co-polymeric beads prepared from at least one monomer and at least one porogen, the beads being cross-linked with a polyethylenically unsaturated monomer, the beads having a continuous network of interconnecting pores, comprising macropores; mesopores, micropores of <20 Å diameter, and gel porosity, and wherein the at least one active ingredient is contained within the network of pores; and applying the mixture in fluid or gel form to a surface, thereby forming a film coating, which continuously transports outward the at least one active ingredient by internal flow within the network of pores, resulting in delivery from the macropores to the coated surface for a sustained time of at least 24 hours from application, and wherein the network of pores is non-collapsible upon removal of the active ingredient.

2. The method of slow-release delivery of claim 1, wherein the at least one active ingredient is further released by internal flow over a period of time, extending from at least 24 hours to at least 48 hours.

3. The method of slow-release delivery of claim 1, wherein the at least one active ingredient is further released by internal flow over a period of time, extending from at least 24 hours to at least 5 days.

4. The method of slow-release delivery of claim 1, wherein the at least one active ingredient is further released by internal flow over a period of time, extending from at least 24 hours to at least 10 days.

5. The method of slow-release delivery of claim 1, wherein the at least one active ingredient is further released by internal flow over a period extending from at least 24 hours to at least 20 days.

6. The method of slow-release delivery of claim 1, wherein the at least one active ingredient is further released by internal flow over a period of time, extending from at least 24 hours to at least 1 month.

7. The method of slow-release delivery of claim 1, wherein the at least one active ingredient is further released by internal flow over a period of time, extending from at least 24 hours to at least 1 year.

8. The method of slow-release delivery of claim 1, wherein the at least one active ingredient is further released by internal flow over a period of time, extending from at least 24 hours to more than 1 year.

9. The method of claim 1, wherein the at least one active ingredient enters the pore network by contact absorption.

10. The method of claim 9, further comprising dissolving the at least one active ingredient in a solvent prior to absorption.

11. The method of claim 9, further comprising removing the solvent from the bead that was used to deliver the at least one active ingredient, and repeating contact absorption of the at least one active ingredient to increase the concentration of the at least one active ingredient in the pore network.

12. The method of claim 1, wherein the porogen is not removed from the beads.

13. The method of claim 12, wherein the porogen comprises the at least one active ingredient.

14. The method of claim 1, wherein the mixture further comprises a plasticizer.

15. The method of claim 14, wherein the plasticizer comprises the at least one active ingredient.

* * * * *